(12) United States Patent
Nafpliotis

(10) Patent No.: US 6,364,851 B1
(45) Date of Patent: Apr. 2, 2002

(54) BIOMECHANICAL SUIT

(76) Inventor: Harry Nafpliotis, 15 Rising Ridge Rd., Upper Saddle River, NJ (US) 07548

( * ) Notice: Subject to any disclaimer, the term of this patent is extended or adjusted under 35 U.S.C. 154(b) by 0 days.

(21) Appl. No.: 09/266,662

(22) Filed: Mar. 11, 1999

(51) Int. Cl.[7] ............................ A61F 5/00; A61F 13/00; A41D 1/00
(52) U.S. Cl. ............................ 602/19; 602/60; 2/69
(58) Field of Search ............................ 2/69, 79, 85, 93, 2/108, 227, 238, 228; 602/18, 19; 482/105, 122, 129

(56) References Cited

U.S. PATENT DOCUMENTS 5,555,562 A * 9/1996 Holt et al. .................... 2/69
5,842,959 A * 12/1998 Wilkinson .................. 482/121
5,937,441 A * 8/1999 Raines ........................... 2/69

* cited by examiner

Primary Examiner—Kim M. Lewis
(74) Attorney, Agent, or Firm—Richard A. Joel, Esq.

(57) ABSTRACT

A biomechanical suit comprises a body suit of a material such as Lycra® or Spandex® or a combination with polyester which includes a plurality of weighted pockets located posterolaterally for enhancing muscle balance to provide good posture and cardiovascular fitness. The suit extends proximally from the neck at the level of throat flexure anteriorly. A plastic zipper extends from the umbilicus to the proximal anterior attachment at the neck. Posteriorly, the suit extends from the C-3 level and includes a plurality of specifically positioned pockets to receive predetermined weights which also provide resistive exercises for fitness purposes.

7 Claims, 2 Drawing Sheets

BIOMECHANICAL SUIT

CROSS-REFERENCE TO RELATED APPLICATIONS

None

STATEMENT REGARDING FEDERALLY SPONSORED RESEARCH OR DEVELOPMENT

Not applicable.

BACKGROUND OF THE INVENTION

1. Field of the Invention

This invention relates to a biomechanical suit which is intended to correct physical conditions without extensive surgery and/or progressive casting.

2. Description of the Related Art Including Information Disclosed Under 37 CFR §§1.97–1.98

In the prior art, the solution to scoliotic, kyphotic and/or young children's spinal conditions often involved extensive surgery which was at the very least somewhat risky and may or may not have been effective. Another treatment involved progressive casting which was incapacitating and uncomfortable. Further problems of casting include muscle waste, skin break-down, and lack of cleanliness. The casting was either used alone or in conjunction with surgery.

In contrast to the prior art, applicant's biomechanical suit provides a training pattern to correct posture problems and physical problems while at the same time promoting cardiovascular fitness. The suit in many cases, eliminates the need for surgery or incapacitating casting. The biomechanical suit is also easy to wear and rather comfortable. It is a considerable improvement over the antiquated techniques of the prior art and at a much lower cost.

SUMMARY OF THE INVENTION

This invention relates to biomechanical suits and particularly to a body suit of material such as Lycra® or Spandex® or a combination with polyester. The suit includes weighted pockets located posterolaterally for enhancing muscle balance and for effectuating good posture and cardiovascular fitness.

The suit extends proximally from the neck at the level of throat flexure anteriorly. A plastic zipper extends from the umbilicus to the proximal anterior attachment. Posteriorly, the suit extends from the C-3 level to wrap around an individuals buttocks and connect with the forward portion through the crotch.

The suit includes short sleeves and a plurality of pockets on the posterior side. Eight pockets with Velcro® closures are positioned on the posterior side of the suit. The pockets are 4–6 inches in length and weights of ½–2 pounds may be inserted in the pockets depending upon the postural integrity diagnosis. Two additional pockets may be included for additional weights based upon an individuals height, weight, degree of fitness and the problem involved. The suit corrects a number of physical problems in an inexpensive and non-invasive manner.

Accordingly, an object of this invention is to provide a new and improved biomechanical body suit to correct physical problems.

Another object of this invention is to provide a new and improved biomechanical body suit which improves health by providing a cardiovascular workout.

A further object of this invention is to provide a new and improved biomechanical body suit of a specific material which extends about an individual's upper torso and includes a plurality of posterior spaced pockets to receive corrective weights.

Additionally, in view of the enhancement for correct body mechanics, another object of this invention is to provide relief from lower back pain stemming from poor posture.

A more specific object of this invention is to provide a new and improved biomechanical body suit which extends from the C-3 level posteriorly and about an individual's upper torso with a plurality of spaced pockets having Velcro® closures to receive predetermined weights in order to correct posture and various medical painful conditions while providing a cardiovascular workout.

BRIEF DESCRIPTION OF THE DRAWINGS

The above and other objects and advantages of this invention may be more clearly seen when viewed in conjunction with the accompanying drawings wherein.

DETAILED DESCRIPTION OF THE INVENTION

Figure 1:
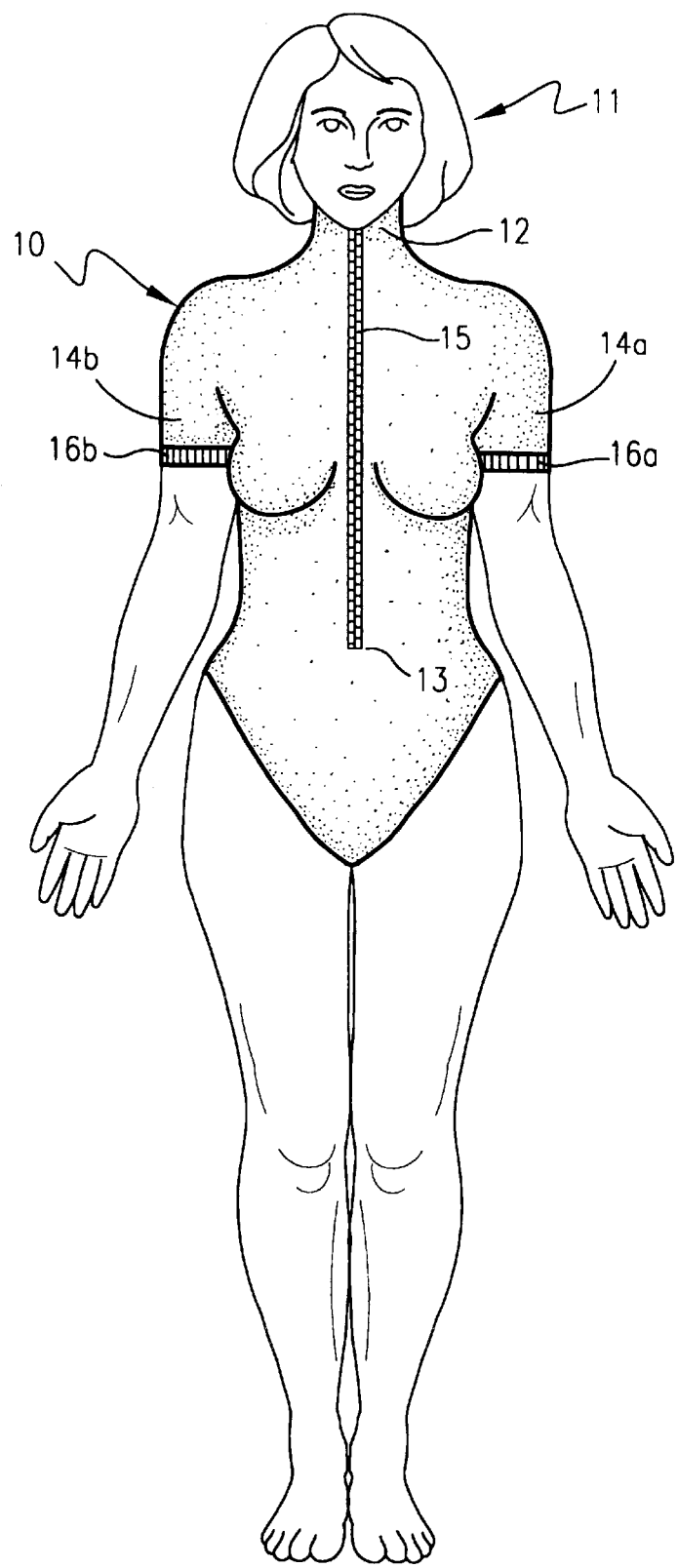
FIG. 1 is a front or anterior view of the invention.
Figure 2:
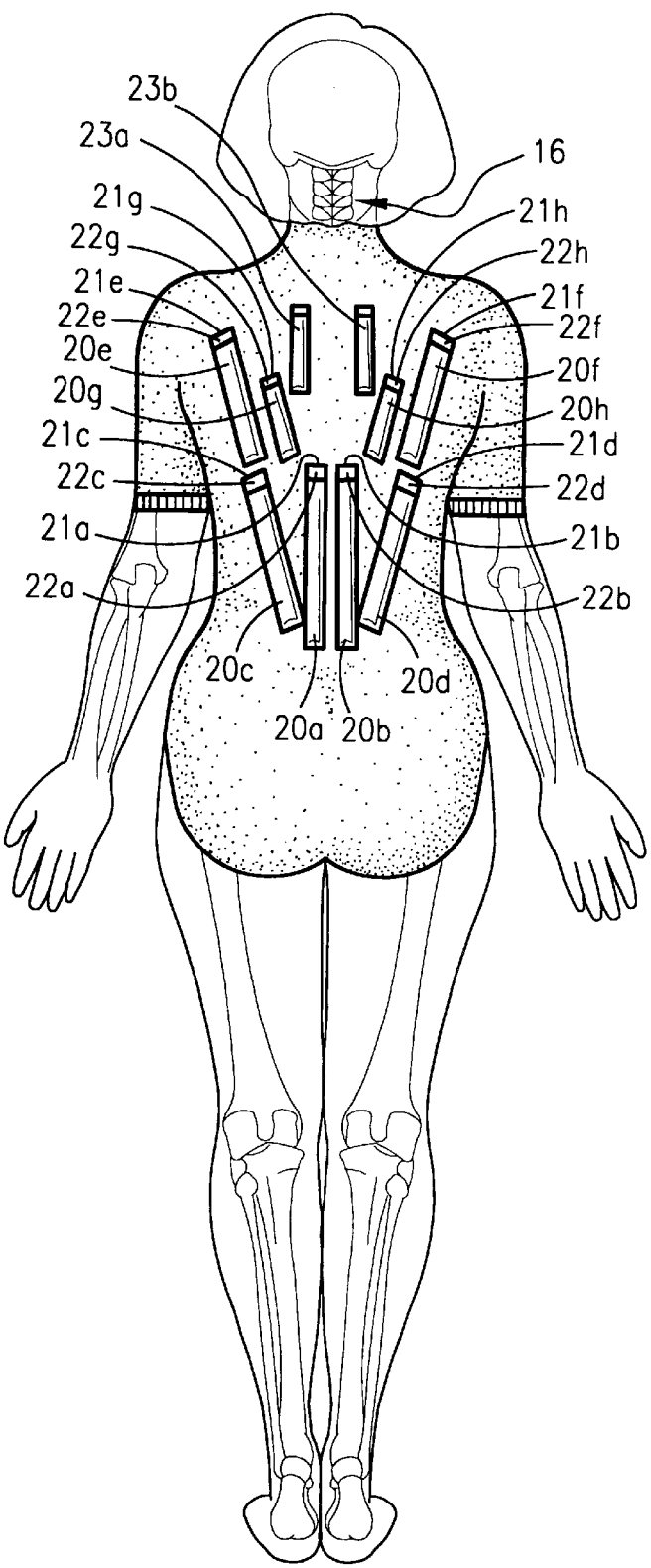
FIG. 2 is a rear or posterior view of the invention.

Referring now to the drawings FIG. 1 discloses an anterior view of the body suit 10 worn by an individual 11. The suit 10 extends proximately from the neck at the level of throat flexure 12 anteriorly and includes a plastic zipper 15 which extends from the lower lever 13 adjacent the umbilicus to the proximate anterior level 12. The shirt includes short sleeves 14a and 14b with elastic straps 16a and 16b for firmness.

The body suit 10 is made of Lycra, Spandex, canvas, neoprene or a combination of such materials with polyester. The suit 10 is designed to enhance correct body mechanics, condition upper and lower extremities' musculature, and improve cardiovascular fitness with progressive use of weights during aerobic activity. The suit 10 also corrects poor spinal posture conditions such as scoliosis, round shoulders and kyphosis, and relieves pain stemming from poor body mechanics, if used early enough, by transposing the weights posteriorly.

The body suit 10 extends from the cervical three (C-3) vertebra level 16 and a plurality of posterior pockets 20a–h, four to six inches in length with open ends 21a–h two inches wide, for the insertion of silicon/lead tubes (not shown) weighing one to two pounds. Velcro® closures 22a–h are provided to secure the tubes within pockets 21a–h. The pockets 20a and 20b are positioned vertically adjacent the spine while adjacent pockets 20c and 20d flare outwardly at their upper ends. Additional pockets 20e and 20f with smaller pockets 20g and 20h flare outwardly at the cephalocaudal extent T2-L-4.

Two optional upper posterior pockets 23a and 23b may be provided each on opposite sides of the spine depending upon an individual's measurements. The criteria would involve height, weight, and degree of physical fitness. The body suit 10 provides resistive exercises using silicon/lead tubes in a training pattern to prevent and remedy spinal conditions without extensive surgery and progressive casting. The biomechanical suit 10 provides a less costly alternative to surgery.

While the invention has been explained by a detailed description of certain specific embodiments, it is understood that various modifications and substitutions can be made in any of them within the scope of the appended claims which are intended also to include equivalents of such embodiments.

What is claimed is:

1. A one piece biomechanical body suit worn by individuals to correct physical posture problems by transposing weights in the suit on selected sides of the vertebral column to overcome said problems without the necessity of surgery comprising:

an upper portion extending upwardly about the neck at the level of throat flexure anteriorly;

an intermediate portion having a body portion including a pair of sleeves;

a lower portion having leg openings;

a zipper extending from the proximal anterior level at the neck to the area of the umbilicus;

a posterior section of the intermediate portion having a plurality of discontinuous spaced pockets, two of said pockets being parallel and vertically extending adjacent the vertebral column for a predetermined distance with one pocket on each side of said column and a pair of pockets flaring outwardly from the base of the vertebral column on each side thereof; and a plurality of weights, each to be inserted in a pocket to enhance muscle balance, and promote good posture and cardiovascular fitness.

2. A one-piece biomechanical body suit worn by individuals to correct physical posture problems in accordance with claim 1, wherein:

the suit includes ten pockets five on each side of the vertebral column, each having Velcro® closures or other materials to facilitate correct positions of the weights.

3. A one piece biomechanical body suit worn by individuals to correct physical posture problems in accordance with claim 2, wherein:

the pockets are 4 to 6 inches in length; and the weights range from ½ to 2 pounds as determined by the condition to be corrected.

4. A one piece biomechanical body suit worn by individuals to correct physical posture problems in accordance with claim 1, wherein:

the suit is comprised of a polyester, fleece, micro fiber nylon, canvas, or neoprene material.

5. A one piece biomechanical body suit worn by individuals to correct physical posture problems in accordance with claim 3, wherein:

two additional smaller pockets are provided adapted to extend one on each side of the vertebral column above the two parallel pockets.

6. A one piece biomechanical body suit worn by individuals to correct physical posture problems in accordance with claim 5, wherein:

the pockets are each two inches wide and the weights are silicon or small lead spheres.

7. A one-piece biomechanical body suit worn by individuals to correct physical posture problems in accordance with claim 2, wherein:

the flaring pockets are substantially parallel on each side of the vetebral column and further include two upper pockets on each side located at the cephalocaudal extent and the interior of said pockets is smaller than the exterior pocket and wherein the suit provides relief from spinal pain resulting from poor posture.

* * * * *